United States Patent [19]

Karabegov et al.

[11] 4,380,392
[45] Apr. 19, 1983

[54] METHOD AND APPARATUS FOR CALIBRATION OF INSTRUMENTS SERVING TO COUNT AND TO DETERMINE THE SIZE OF PARTICLES SUSPENDED IN DISPERSION MEDIUM

[76] Inventors: Mikhail A. Karabegov, ulitsa Mardzhanishvili, 35; Aram G. Ovanesian, ulitsa Sundukiana, 22; Eduard A. Mesropian, prospekt Plekhanova, 151; Georgy T. Metreveli, Gldansky massiv, 7 mikroraion, 10 korpus, kv. 153; Anatoly A. Karpeev, Kakhetinskoeshosse, 38; Boris K. Khoshtaria, ulitsa Dadiani, 8; Tatyana I. Gventsadze, ulitsa Kamo, 79/81, kv. 19, all of Tbilisi, U.S.S.R.

[21] Appl. No.: 245,122

[22] Filed: Mar. 18, 1981

[51] Int. Cl.³ .............................................. G01B 11/10
[52] U.S. Cl. ..................................... 356/243; 356/336
[58] Field of Search ....................... 356/243, 335, 336; 250/564, 565, 573, 574, 222 PC

[56] References Cited

U.S. PATENT DOCUMENTS 3,127,464  3/1964  Gustavson ...................... 356/243 X
4,135,821  1/1979  Pechin et al. ................... 356/243 X

FOREIGN PATENT DOCUMENTS 2022282  12/1979  United Kingdom ............... 356/243

Primary Examiner—John K. Corbin
Assistant Examiner—Matthew W. Koren
Attorney, Agent, or Firm—Burgess, Ryan and Wayne

[57] ABSTRACT

An instrument for counting and determining the size of particles suspended in a dispersion medium is calibrated by setting a certified particle contained in the dispersion medium in motion so that the particle repeatedly crosses the sensing zone of the instrument under calibration. An apparatus for accomplishing the calibration method comprises a vessel wherein a dispersion medium and a certified particle are placed and an actuator to set the certified particle in motion whereby a disperse system flow is simulated. Passing a flux of a radiant energy, such as light, through the dispersion medium gives rise to radiation pulses which are used as a basis to set the threshold of sensitivity of the instrument under calibration.

11 Claims, 6 Drawing Figures

METHOD AND APPARATUS FOR CALIBRATION OF INSTRUMENTS SERVING TO COUNT AND TO DETERMINE THE SIZE OF PARTICLES SUSPENDED IN DISPERSION MEDIUM

BACKGROUND OF THE INVENTION

1. Field of the Invention

The present invention relates to the field of instrument engineering and is specifically concerned with a method and apparatus for calibration of instruments used to count and to determine the size of particles suspended in dispersion media.

The invention may find a successful application in essentially all the fields where determining the size distribution of particles suspended in transparent dispersion media is needed. It may be particularly useful in the chemical, petroleum processing, and pharmaceutical industries for monitoring environmental pollution, contamination of production-process media, and determining the concentration of a suspended product.

2. Description of the Prior Art

The manufacture of novel products, introduction of novel production processes, and implementation of environmental protection programs which involve monitoring the contamination of sewage water and other production-process media by various production wastes as well as analyzing the particle size of plankton in open basins greatly extended the range of disperse systems where the particle size distribution is to be checked promptly.

Thus, for example, in the production of suspended plastics, such as polyvinyl chloride, polymethyl methacrylate, etc., the used disperse fluid is drained at the end of the production process; some amount of the product may remain in the liquid, which may result in contamination of water basins. This necessitates the provision in the production line of an instrument to monitor the concentration of the initial product, contaminating the flow, in order to determine whether the liquid is to be refiltered. Such urgent problems as monitoring the performance of filters for specific media, determining the fineness of grinding of abrasive and other powders, analyzing the particle size of plankton, determining the degree of contamination of various production-process flows by particles of the product being made, as well as monitoring the contamination of hydraulic fluids by particles resulting from wear of rubbing parts are at present solved rather approximately, with an inadequate accuracy, and in many instances still remain to be solved.

Among analytical methods for determining the particle size distribution, an extensive application is at present found by photometric-counting analysis techniques, based on determining the particle size by measuring the amplitudes of electric pulses produced at the photodetector output whenever the particles pass through an illuminated sensing zone. Inasmuch as the measurement is accomplished indirectly, its results depend on the optical properties of the medium under analysis, and therefore the instruments of this type must be calibrated against standard media whose optical properties are identical to those of the medium to be analyzed. The range of calibration monodisperse media known at present is quite limited: latexes; dental powders; glass beads; melamine-formaldehyde resin suspensions. Preparing monodisperse calibration media of a predetermined origin involves complex and labour-consuming processes and in some cases is impossible at all. This considerably restricts the range of media analyzed by photometric-counting instruments.

The restrictions hold also for other counting methods of particle size analysis, such as gravimetric, conductometric, dielcometric, etc.

When no standard media are available, the results of a particle size analysis are arbitrary. If, for example, an instrument has been calibrated with standard particles of glass, then analyses of disperse media where particles of another origin, such as rubber, are present will yield wrong results. To obtain reliable results in such events, labour- and time-consuming microscopic analysis techniques must be resorted to in practice.

A calibration method has been proposed, based on passing calibration media through the illuminated sensing zone of an instrument (Standards for the calibration of automatic particle counters. "Hydraulics and Pneumatics", July, 1955).

Calibration media are prepared from initial standard ones. To this end, a weighed quantity with the same distribution of dispersed phase particles as in the dispersed phase of the standard media is taken from the total mass of particles (or suspension). The part thus taken is diluted in a dispersion medium of a certain volume to obtain the predetermined concentration. The error in preparing a calibration medium of the predetermined concentration depends on the degree of "monodispersity" of dispersed phase particles. The higher the monodispersity, the less particles whose size differs from the average one are in the medium and hence the more accurately the quantity $N_o$ of dispersed phase particles can be determined from the weight or volume of the standard (primary) medium.

The calibration medium thus prepared, which contains a known quantity (determined to within a few percent) of particles of a certain size (in fact, of a range of sizes), is then passed through the sensing zone of the instrument under calibration.

The apparatus should count the number of crossings of the sensing zone by the particles; as the total volume of the calibration medium has been passed through the sensing zone, a number $N_1$ of pulses which coincides with or is close to the calculated one should be recorded at the recorder output. The sensitivity of the instrument is set so that all the pulses be counted at the threshold being calibrated. It this is not the case, the sensitivity is readjusted until the condition is satisfied.

The highest calibration accuracy is attained with the use of strictly monodisperse standard media.

Unfortunately, no strictly monodisperse media are at present available for the range of media being analyzed, and this makes it difficult to set the threshold of sensitivity of an instrument being calibrated.

There is known a limited range of monodisperse media with particles of various origin, which restricts the field of application of instruments of the above-mentioned purpose.

When stored, the known monodisperse media may coagulate, give rise to aggregates, which changes the value of the certified parameter, and therefore must be periodically re-certified for their re-use as standard ones. Periodical calibration of the instruments' thresholds is needed due to a possible change in the rating of a parameter of one of instrument's units as well as in carrying out preventive and scheduled maintenance jobs.

A grave disadvantage of the method lies in that the calibration process is laborious and takes a long time; this impedes periodical checkout of the stability of thresholds as well as automation of calibration in the field.

Another method for calibration of instruments used in particle counting and sizing applications has been reported in "Journal of the Air Pollution Control Association", October 1968, vol. 18, No. 10, p. 658.

In this method, calibration of an instrument is based on modulating a flux of radiation taken from the port of the illuminator of the instrument under calibration, the modulated flux being directed onto the photodetector of the apparatus; the modulation is accomplished through interrupting the light flux by a rotating disk with calibrated apertures. Rotation of the disk produces a regular sequence of pulses with a certain amplitude, which are used as a basis to readjust the threshold of sensitivity of the instrument being calibrated. Bringing the threshold sensitivity into accordance with a certain particle size is accomplished by a primary calibration with the use of standard monodisperse media.

The primary calibration (of the modulator) proceeds as follows. Calibration media are prepared from standard ones and passed through instruments. An instrument counts the number of crossings of the sensing zone by particles, and a number of pulses whose amplitude is proportional to the size of corresponding particles in the calibration medium will be recorded at the output.

The sensitivity of the instrument is set such that particles of a certain size be recorded at a certain value of the sensitivity threshold. At the same value of sensitivity, the pulses from the modulator have a certain amplitude which is memorized in an electronic unit of the instrument.

The primary calibration of the modulator against standard media is carried out whenever a change in parameters or characteristics of the instrument's units is possible, such as in case of a failure and replacement of the radiation source or receiver, realignment, a change in parameters of the sensitive volume fouling of optical elements, etc.

The pulses from the modulator should in the course of operation have the same amplitude as in the primary calibration. Thus, the threshold sensitivity of an instrument is in the course of operation checked and readjusted against the pulses from the modulator.

However, this method for calibration of particle counting and sizing instruments suffers from a number of disadvantages.

The modulator promotes detecting and compensating for general changes in the instrument's parameters (e.g. a change in the radiation flux, fouling of optical elements, a change in the recorder's sensitivity), but is incapable of revealing possible local variations or redistributions of the illuminance in the sensing zone, which may arise in the course of operation, such as contaminations of the tray walls, existence of dark zones, due to a realignment, etc.

To analyze media of a certain origin, the modulator (the instrument's sensitivity) must be calibrated against monodisperse calibration media of the same origin. For another parameters or origin of the medium under analysis, the instrument readings will be not true. It follows that to obtain reliable particle size analysis results, the instrument must be calibrated against standard calibration media where the dispersion medium and the dispersed phase have the same properties as does the medium under analysis; but this is attainable very infrequently because of a limited range of standard systems, which narrows the field of application of such instruments.

When monodisperse standard media are available, the modulator is calibrated by comparing in amplitude the pulses from particles in the calibration media with the pulses of the modulator. The higher the degree of monodispersity of particles, the simpler and more accurate is the calibration process. No strictly monodisperse calibration media exist, however, and therefore the calibration is based on the average size of dispersed phase particles, obtained by statistically averaging the sizes of a great quantity of particles; this gives rise to a certain error in the primary calibration of the threshold of sensitivity of an instrument and of an modulator.

SUMMARY OF THE INVENTION

An object of the present invention is to provide a method and an apparatus for calibration of instruments serving to count and to determine the size of particles suspended in dispersion media.

Another object of the invention is to provide a method and an apparatus, which allow to both cut down the labour consumption and simplify the process of calibration of instruments serving to count and to determine the size of particles suspended in dispersion media.

Still another object of the invention is to provide a method and an apparatus, which allow to upgrade the accuracy of calibration of instruments serving to determine the particle size distribution in disperse systems.

More specifically, the object of the present invention consists in the provision of a method and of a calibrator, which by means of simulating calibration disperse systems of a predetermined size make it possible to simplify the calibration process, cut down the labour consumption, and upgrade the accuracy of calibration of instruments serving to determine the particle size distribution in disperse systems.

The above-mentioned and other objects are attained by that in a method for calibration of an instrument serving to count and to determine the size of particles suspended in a dispersion medium and consisting in that a flow of a calibration disperse system is passed through the sensing zone of the instrument under calibration and the radiation pulses obtained in this process are used as a basis for setting the threshold of sensitivity of the instrument, according to the invention, a certified particle is taken and moved in the dispersion medium in such a manner that the particle repeatedly crosses the sensing zone of the instrument, whereby the passing of a disperse system flow is simulated.

Such a method makes it possible to upgrade the accuracy a calibration of an instrument used to count and to determine the size of particles suspended in dispersion media, since a repeated crossing of the sensing zone by one and the same certified particle gives rise to a sequence of pulses with a strictly indentical amplitude. This, in its turn, permits standardization of the sensitivity thresholds of instruments of the same type as well as allows the rated sensitivity of an apparatus to be restored in the field after a preventive maintenance and a realignment of the instrument's primary transducer.

The above-mentioned and other objects are attained also by the provision of an apparatus for calibration of instruments serving to count and to determine the size of particles suspended in dispersion media, which instruments include a radiation source and a radiation receiver having a sensivity threshold, with a sensing zone in between, and which instruments comprising a modulator of the radiation passing through the sensing zone of the instrument under calibration, in which apparatus, according to the invention, the modulator has the form of a vessel serving to place therein a dispersion medium with one certified particle and includes an actuator to set the particle in motion so that it repeatedly crosses the sensing zone of the instrument under calibration, whereby a flow of a disperse system through the sensing zone of the instrument is simulated.

Such an apparatus allows to considerably simplify the process as well as upgrade the accuracy of calibration owing to a possibility of moving a certified particle so that it repeatedly crosses the instrument's sensing zone, which provides a simulation of a disperse system flow.

The actuator to move a certified particle advantageously has the form of a vibrator which interacts with the bottom of said vessel, having the form of a flexible diaphragm.

The certified particle may be reciprocated; this will simplify both the general arrangement and the design of the apparatus.

It is advisable to optically magnify the sensing zone and to pass the certified particle across an enlarged image of the zone.

A magnification of the image of the sensing zone of an instrument for counting and determining the size of particles suspended in a dispersion medium (referred to hereinafter simply as "instrument" for brevity) simplifies the preparation procedure and extends the potentialities of the calibration process.

This makes it possible to place a certified particle, enlarged n times, into a sensing zone, magnified n times. The possibility of using a larger-size certified particle simplifies its manufacture. Moreover, a single certified particle can then be used for calibration of several size discrimination thersholds of an instrument—appropriately varying, of course, the magnification of the sensing zone.

While offering a fairly simple construction, such an apparatus provides the possibility of moving a certified particle of substantially any origin.

When a certified particle is of a magnetic material, the particle-moving actuator is preferably given the form of an electromagnet with a variable field wherein said vessel is disposed.

Although an electromagnetic actuator is capable of moving only magnetic particles, such as apparatus offers a higher dependability owing to elimination of mechanical effects upon the apparatus' components and also allows to increase the frequency of certified particle oscillations.

It is advisable that said vessel be provided in its bottom part with a flare and that perforated partitions or screens be installed in the vessel's inner space above and below the sensing zone in order to limit the travel of a certified particle placed therebetween.

A flared bottom part of the vessel increases the area of the vessel's bottom and hence allows the travel of a certified particle and a dispersion medium, which are in the vessel, to be extended without increasing the effort and stroke of the actuator (vibrator), while the screens inside the vessel ensure keeping the certified particle within the region of the sensing zone.

The vessel may be provided with two oppositely disposed flexible diaphragms and the actuator may in this case take the form of two vibrators, either of which is fitted to its corresponding diaphragm.

Such a configuration of the apparatus allows a certified particle to be reciprocated at the same speed in the forward and reverse directions, which upgrades the accuracy of calibration owing to the same duration of the calibrating pulses produced in this case.

BRIEF DESCRIPTION OF THE DRAWINGS

The invention will now be explained by a detailed description of a method for calibration of an instrument serving to count and to determine the size of particles suspended in dispersion media as well as by a detailed description of an apparatus therefore with reference to the accompanying drawings where identical parts are designated by identical reference numerals and in which.

DETAILED DESCRIPTION OF PREFERABLE EMBODIMENTS OF THE INVENTION

Figure 1:
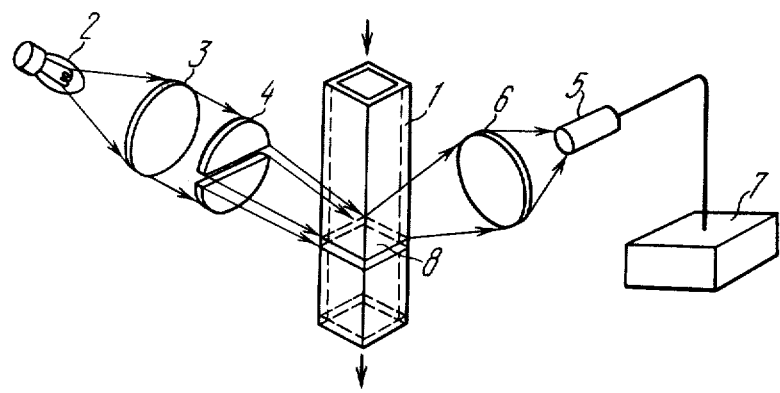
FIG. 1 is a diagrammatic view of an instrument for counting and determining the size of particles suspended in a dispersion medium in the course of analyzing the medium passing through a transparent square channel.

Referring to FIG. 1, a traditional instrument for counting and determining the size of particles suspended in dispersion media (referred to as "instrument", as indicated above) comprises an illuminator system, a radiation receiver system, and an electronic unit. A transparent channel 1 for moving the disperse system under analysis is disposed between the illuminator system and the receiver system.

The illuminator system comprises a light source, such as a halogen lamp 2, a positive lens 3 to shape a directional radiation flux from the light source, and a field diaphragm 4 disposed downstream (with respect to the beam travel direction) of the lens 3.

The radiation receiver system includes a radiation receiver 5 proper, upstream (with respect to the radiation flux direction) of which a lens 6 is installed to direct the radiation flux onto the inlet port of the receiver 5.

The receiver 5 is connected to the input of an electronic unit 7.

The instrument has a sensing zone 8 formed in a known manner.

According to the prior art, a calibration disperse system against which the instrument was calibrated was fed through the channel 1.

Figure 2:
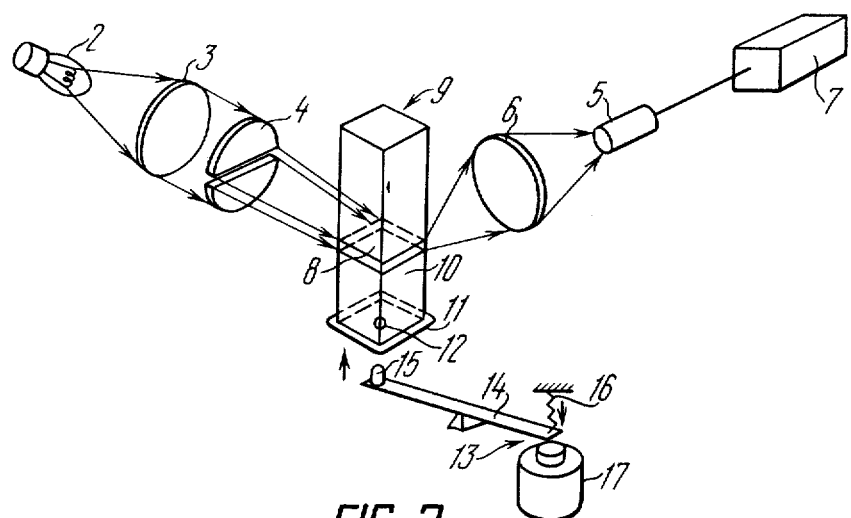
FIG. 2 is a diagrammatic view of a calibration apparatus disposed in the region of the sensing zone of the instrument.

According to the present invention, the instrument is calibrated with the aid of an apparatus 9 which simulates the flow of a disperse system. The apparatus 9 (FIG. 2) is installed in place of the working channel 1.

The apparatus 9 for calibration of the instrument comprises a modulator of the radiation passing through the sensing zone of the instrument under calibration. The apparatus 9 has the form of a rectangular transparent vessel 10 with a bottom 11.

The vessel 10, whose cross-sectional size and shape are essentially the same as those of the channel 1, serves to place therein a dispersion medium containing one certified particle 12. The apparatus 9 has an actuator to set the particle in motion so that it repeatedly crosses the sensing zone 8 of the instrument under calibration. The particle 12 may pass through the sensing zone 8 under various laws of its motion, such as executing circular movements along an orbit inclined at an angle to the vessel's vertical axis or a reciprocating movement up and down, etc.

The invention will be explained for a reciprocating certified particle.

In an embodiment of the invention, the actuator for reciprocating the certified particle 12 in the vessel has the form of a vibrator 13 including a rocker 14 whose one end is provided with a hammer 15, while the other end is coupled with a spring 16 and interacts with a solenoid 17.

The apparatus 9 constructed in accordance with the above-described embodiment of the invention functions as follows.

When the solenoid 17 is energized, the rocker 14 oscillates and strikes by the hammer 15 the bottom 11 of the vessel 10. The inertial force causes the certified particle 12 to jump up, following which the gravity causes it to fall down on the bottom 11 of the vessel 12. Reciprocating in such a manner, the certified particle 12 repeatedly crosses the sensing zone 8 of the instrument. Repeatedly oscillating, the particle 12 disperses the light flux into momentary light flashes which are transformed by the receiver 5 into electric pulses. The pulses are applied to the input of the electronic unit 7 where the particles are counted in accordance with the respective thresholds of sensitivity of the unit 7 depending on the amplitude of the pulses.

Figure 3:
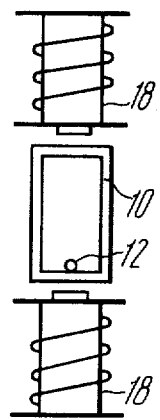
FIG. 3 is a diagrammatic view of an apparatus with an actuator in the form of an electromagnet.

In another embodiment of the invention, the actuator for moving a dispersion medium and the certified particle 12 in the vessel 10 (FIG. 3) has the form of an alternating-current electromagnet, into whose field the vessel 10 is placed. The electromagnet is composed of solenoids 18 disposed at both sides of the ends of the vessel 10 which is closed from above by a cover.

According to the another embodiment of the invention, the process of calibration and the operation of the apparatus 9 proceed in the same manner as described above, the only difference being that the certified particle 12 reciprocates up and down under the action of the alternating electromagnetic field; of course, the certified particle 12 must in this case have magnetic properties.

Figure 4:
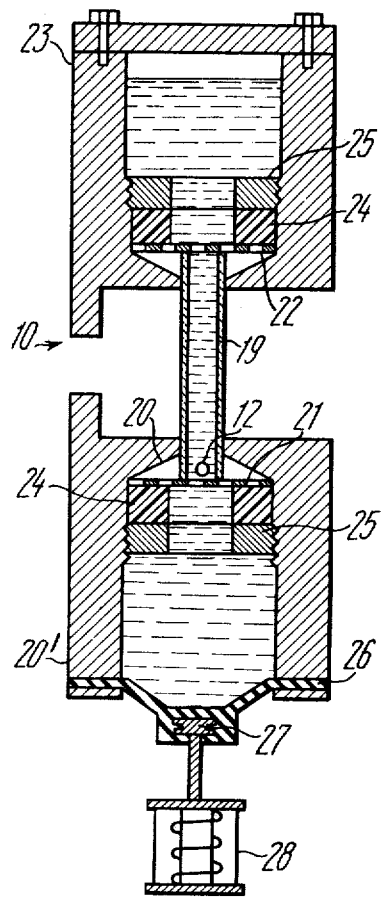
FIG. 4 shows another modification of the apparatus, provided with a flare in the bottom part and with screens in the middle part.

In a still another embodiment of the invention, the vessel 10 of the apparatus 9 has the form of a vertical tube 19 (FIG. 4) with a flare 20 at least in the bottom part. Perforated partitions 21 and 22 are built into the inner space of the vessel 10 above and below the sensing zone to restrict the travel of a certified particle placed therebetween. Referring to FIG. 4 which shows an apparatus constructed in accordance with this embodiment of the invention, the vessel 10 has taken the form of square-section transparent tube 19 whose ends are adjoined by flares in the form of sleeves 20' and 23 encompassing respectively the ends of the tube 19. The perforated partitions 21 and 22 are disposed inside the sleeves 20' and 23 and pressed against the end faces of the tube 19 by elastic gaskets 24 and nuts 25. The sleeve 23 is closed by a cover, while the sleeve 20' is closed by a flexible diaphragm 26 whereto a core 27 of a solenoid 28 is attached.

Reciprocation of the core 27 of the solenoid 28 causes the diaphragm 26 to move the dispersion medium (liquid) with the certified particle 12 to and fro, while the perforated partitions 21, 22 keep the certified particle 12 within the height of the tube 19, preventing the particle from getting into one (e.g. lower) flare 20 and hence from leaving the region of the sensing zone of the apparatus 9. The provision of the flares 20, 23 results in a considerable travel of the certified particle 12 at a small travel of the core 27 of the solenoid 28.

In the next embodiment of the invention, the vessel 10 takes the form of a tube 29 (FIG. 5) closed at both ends by flexible diaphragms 30 and 30' which are adjoined by vibrators each in the form of a solenoid 31 and 31'. Cores 32 of the solenoids 31 are attached to the flexible diaphragms 30. Perforated partitions 33 which restrict the travel of the certified particle 12 up and down with respect to the sensing zone 8 of the instrument and the ends of the tube 29 are in the form of flares 34 and 35.

When the solenoids 31 are alternately activated, the certified particle 12, entrained by the dispersion medium, moves up and down, crossing repeatedly the sensing zone of the instrument. Calibration of the instrument proceeds in the same manner as described above.

Figure 6:
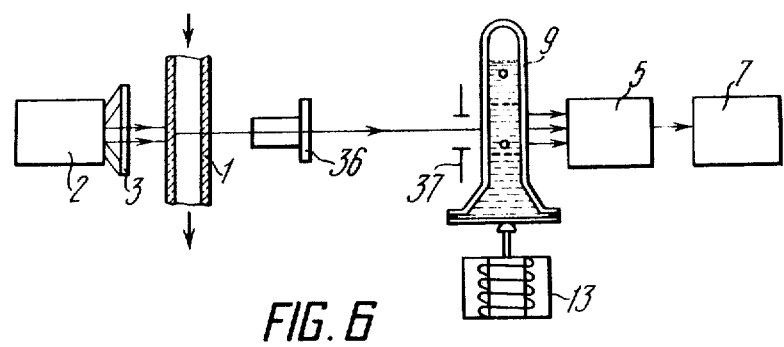
FIG. 6 diagrammatically illustrates a modification of the calibration process, wherein the calibration apparatus is disposed in an enlarged image of the sensing zone of an instrument.

In a still another embodiment of the invention, the sensing zone 8 of the instrument under calibration is optically magnified and a certified particle is passed through the enlarged image of the zone. To realize such an embodiment of the invention, the instrument and the apparatus 9 are disposed as shown in FIG. 6 which is in part identical to FIG. 1, the difference being in that a lens 36 is installed behind the sensing zone 8 formed in the channel 1 wherethrough the disperse system being analyzed is passed. The lens 36 serves to produce an intermediate enlarged image of the sensing zone 8. The magnification of the lens 36 is $9\times$. Thus, if an illuminated sensing zone measuring, say, $0.5 \times 0.5 \times 1$ mm is formed in the channel and a filed diaphragm 37 measures $4.5 \times 0.9$ mm, then the enlarged sensing zone will be of $4.5 \times 4.5 \times 0.9$ mm in size. The calibration apparatus 9 whose vessel 10, in accordance with the above-specified dimensions, may have an internal section of $2 \times 2$ mm is installed in the region of the enlarged image of the sensing zone 8. The lens 36 transfers the enlarged image of the sensing zone 8 to the inlet port of the radiation receiver 5. After the calibration is completed, the apparatus 9 is withdrawn, and the pulses from particles of the medium under analysis, flowing through the channel 1, pass through the lenses 3 and 36 to the radiation receiver 5.

Given below are specific examples of the application of the method of the present invention.

EXAMPLE 1

An instrument for counting and determining the size of particles suspended in dispersion media was calibrated with the aim to diagnose the technical condition of hydraulic equipment and to determine the kinetics of wear of rubbing pairs of various mechanisms.

A glass vessel 10 (FIG. 4) of $1.5 \times 1.5$ mm in the section and of a configuration equivalent to an instrument channel 1 wherethrough the medium under analysis flows was filled with gasoline.

Two perforated partitions 21, 22 in the form 40 μm-mesh metal screens, spaced at 5 mm from each other, were installed in the cross-section of the inner space of the vessel 10, and a bronze particle 12 to 80 μm in size (the size of the particle had been determined beforehand to within ±1 μm with the aid of a microscope) was placed between the screens 21, 22. The bottom part of the vessel 20 had the form of a flare 20, the area of whose base was about 300 times greater than the cross-sectional area of the vessel in the region where the certified particle 12 was disposed.

The base of the flare was closed by a rubber diaphragm 26 whereto a core 27 of a solenoid 28 was attached; the solenoid was connected to a generator (not shown) of electric pulses whose frequency was of 10 Hz.

Oscillations of the core 27 were through the flexible diaphragm 26 transmitted to gasoline, and the latter was alternately forced out of the flare 20 into the narrow-section part of the vessel 10, i.e. into the tube 19, and returned back. Such oscillations of gasoline caused the bronze particle 12, disposed on the lower screen 21, to move towards the upper screen 22 and then to return back under the entraining action of gasoline flow.

The vessel 10 containing the screens 21, 22, the particle 12, and gasoline was jointly with the electromagnetic vibrator 28 installed into the instrument to be calibrated so that the sensing zone 8 of the instrument was positioned between the screens 21, 22 of the vessel 10.

Oscillating in the above manner, the particle 12 repeatedly crossed the sensing zone 8, giving rise to a regular sequence of calibration pulses.

The pulses were used as the calibration ones, i.e. as a basis for readjusting the threshold of sensitivity of the radiation receiver of the instrument under calibration.

When calibration of the instrument for another particle size was needed, a particle of an appropriate size was placed into the space confined by the screens 21, 22, and screens with a mesh size less than the particle diameter were installed. The screens are needed to restrict the reciprocating oscillatory travel of the particle so that it will remain within the region of the sensing zone of the instrument under calibration.

This construction may also be used to calibrate instruments for analyzing other disperse systems; to this end, appropriate dispersion medium and particle are introduced into the vessel's inner space.

EXAMPLE 2

An instrument for counting and determining the size of particles suspended in dispersion media was calibrated with the aim to determine by the instrument the concentration of starting material particles in process waste water within a small size range, from 20 μm.

The vessel 10 of (FIG. 2) the apparatus 9 was filled with distilled water wherefrom mechanical impurities were filtered off. A surfactant, such as trisodium phosphate, was added to the distilled water. A polyvinyl chloride particle 12 of 50 μm in size (the particle size was determined beforehand to within ±1 μm with a microscope) was placed in the vessel 10. The electromagnetic vibrator 28 was connected to a generator (not shown) producing electric pulses at a frequency of 5 Hz. The apparatus 9 was placed into the instrument so that the vessel 10 occupied the place of the channel 1, the cross-sectional size and the configuration of the apparatus' vessel 10 being the same as those of the channel 1.

Oscillating pulses from the electromagnetic vibrator 28 were transmitted through the diaphragm 26 to the certified particle 12, causing the latter to move up and down under the inertial forces and gravity.

Crossing the sensing zone 8 by the certified particle gave rise to a sequence of regular calibration pulses serving as a basis for setting the threshold of sensitivity of the radiation receiver 5 of the instrument under calibration.

EXAMPLE 3

An instrument for counting and determining the size of particles in air was calibrated.

Calibration conditions:

| Calibration conditions: | |
|---|---|
| dispersion medium | air |
| certified particle material | corundum |
| certified particle size, μm | 50 ± 1 |
| particle oscillation frequency, Hz | 20 |

The calibration was accomplished with the use of the apparatus shown in FIG. 4, the procedure being the same as in the preceding Examples.

EXAMPLE 4

Instruments for counting and determining the size of particles suspended in a dispersion medium were calibrated with the aim of standardizing the thresholds of sensitivity of photometric counting analyzers.

Calibration conditions:

| Calibration conditions: | |
|---|---|
| dispersion medium | ethyl alcohol |
| certified particle material | stainless steel |
| certified particle size, μm | 200 |
| certified particle oscillation frequency, Hz | 25 |
| spacing of perforated partitions in apparatus, mm | 5 |
| mesh size of perforated partition of apparatus, μm | 100 |

Figure 5:
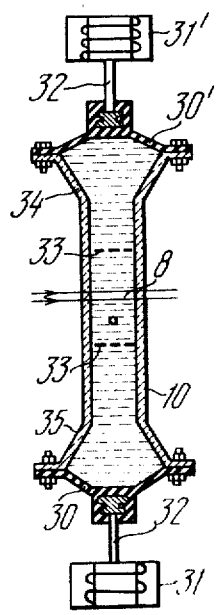
FIG. 5 shows still another modification of the apparatus, having an actuator in the form of two vibrators adjoining oppositely disposed flexible diaphragms.

The instrument was calibrated with the use of the apparatus shown in FIG. 5. The area of the base of flares 34 and 35 of the vessel 10 was about 500 times greater than the cross-sectional area of the vessel in the region of the sensing zone 8. Both electromagnetic vibrators 31 were connected to a generator (not shown) producing phase-shifted electric pulses at a frequency of 25 Hz; thus, when the core 32 of one vibrator 31 was being retracted, the core 32 of the other vibrator 31 was being extended.

The extension of the core from one of the vibrators 31 caused the corresponding diaphragm 30 to flex towards the vessel 10, with the result that the liquid dispersion medium from one flare was forced at a high velocity into the narrow part of the vessel 10. Next, the other electromagnetic vibrator 31' was activated, and the liquid was forced out of the flare 35 in the reverse direction. The reciprocating oscillations of the liquid were transmitted to the certified particle, causing the latter to oscillate in the space confined by the perforated partitions 33.

The modification of the method and apparatus of the invention, presented in this Example, provide a high particle oscillation frequency and the same particle travel speed in the forward and reverse directions. This allows to produce calibration pulses of the same duration and thereby ensures a high calibration accuracy.

What is claimed is:

1. A method for calibrating an optical sensing apparatus which counts particles suspended in a fluid by (i) passing said fluid through a measuring tube having a transparent portion, and (ii) passing a transverse plane of light through said transparent portion of said tube to impinge upon a photodetector, so that particles in said fluid intercept said light and vary the output of the photodetector, said method comprising the steps of:

providing a vertically oriented calibration tube having a transparent portion aligned with said light plane, said calibration tube having closed upper and lower ends and containing a certified particle; and vibrating said lower end of said calibration tube to cause said particle to repetitively intercept said light plane at a predetermined frequency, to cause the output of said photodetector to vary in accordance therewith.

2. A method for calibration as defined in claim 1, where the certified particle is caused to execute a reciprocating motion.

3. A method for calibration as defined in claim 1 or 2, wherein said plane of light is optionally magnified and an enlarged image thereof is intercepted by the certified particle.

4. The method according to claim 1, wherein said otical sensing apparatus produces an enlarged image of said plane of light, and said calibration tube has the transparent portion thereof coincident with said enlarged image.

5. Calibration apparatus for calibrating an optical sensing apparatus which counts particles suspended in a fluid by passing light through the fluid, said calibration apparatus comprising:

a vertically oriented calibration tube having a transparent section for transmitting a beam of light transverse to said tube, said tube having closed upper and lower ends and containing a certified particle;

photo-optical means for generating said light beam and providing an output signal which varies in accordance with variation in the transmissibility through said section of said tube; and means for modulating said output signal by vibrating said lower end of said tube to cause said light beam to be repetitively intercepted by said certified particle.

6. An apparatus as defined in claim 5, wherein said tube is closed at its lower end by a flexible diaphragm and said modulating means comprises a vibrator interacting with the flexible diaphragm of said vessel to impart motion to the certified particle.

7. An apparatus as defined in claim 6, wherein said tube has (i) at its lower end a flare closed by a flexible diaphragm, and (ii) in its inner space, perforated horizontal partitions to restrict the vertical travel of the certified particle.

8. An apparatus as defined in claim 7, wherein said tube has at its upper end a flare closed by a second flexible diaphragm, and another vibrator coupled to said second diaphragm to positively move the certified particle down.

9. The calibration apparatus according to claim 5, wherein said calibration tube is filled with a fluid.

10. The calibration apparatus according to claim 5 or 9, wherein said upper and lower ends of said calibration tube each comprise a flexible diaphragm, and said modulating means comprises means for synchronously vibrating said diaphragms so that they move in opposite directions with respect to said tube.

11. The calibration apparatus according to claim 5, further comprising means for producing an enlarged image of said light beam, said photo-optical means including a photodetector responsive to said enlarged image.

* * * * *